United States Patent [19]

Katunuma

[11] Patent Number: 4,963,654

[45] Date of Patent: Oct. 16, 1990

[54] PEPTIDE SERINE PROTEASE INHIBITOR

[75] Inventor: Nobuhiko Katunuma, Tokushima, Japan

[73] Assignee: Taisho Pharmaceutical Co., Ltd., Japan

[21] Appl. No.: 309,161

[22] Filed: Feb. 13, 1989

[51] Int. Cl.$^5$ ................................................. C07K 7/10
[52] U.S. Cl. .................................................... 530/324
[58] Field of Search ......................................... 530/324

[56] References Cited

U.S. PATENT DOCUMENTS 4,663,437  5/1987  de Bold ................................. 530/324
4,757,048  7/1988  Lewicki et al. ...................... 530/324

Primary Examiner—Lester L. Lee
Attorney, Agent, or Firm—Lorusso & Loud

[57] ABSTRACT

A peptide having an amino acid sequence of the following formula

Ile—Ala—Ala—Cys—Asn—Leu—Pro—Ile—Val—Gln—Gly—
Pro—Cys—Arg—Ala—Phe—Ala—Glu—Leu—Leu—Ala—Phe—
Asp—Ala—Ala—Gln—Gly—Lys—Cys—Ile—Gln—Phe—Ile—
Tyr—Gly—Gly—Cys—Lys—Gly—Asn—Asn—Asn—Lys—Phe—
Tyr—Ser—Glu—Pro—Lys—Cys—Lys—Trp—Tyr—Cys—Gly—
Val—Pro—Gly—Asp—Gly—Tyr is provided as an inhibitor of trypsin and trypsin-like serine proteases.

4 Claims, 1 Drawing Sheet

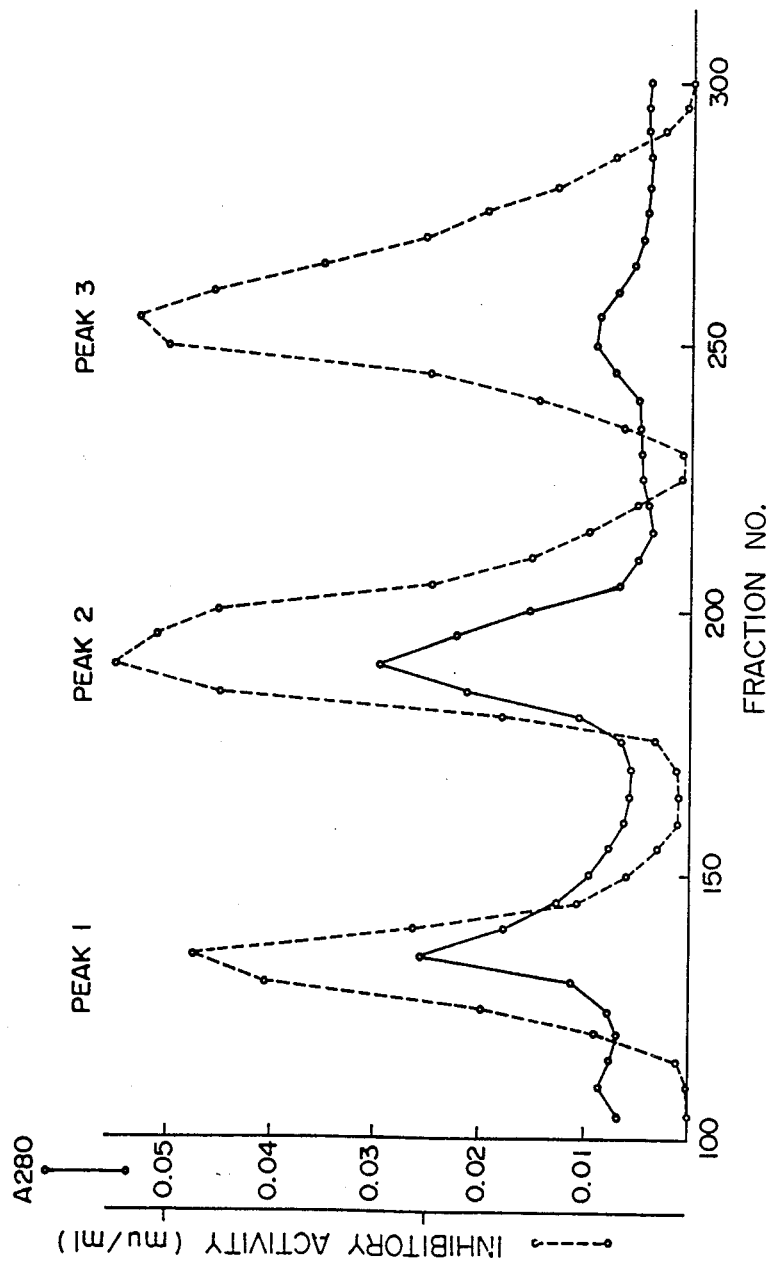
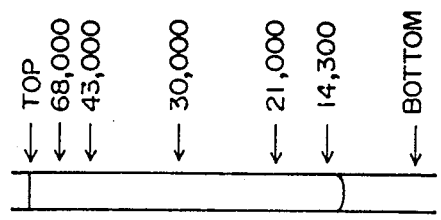

PEPTIDE SERINE PROTEASE INHIBITOR

This invention relates to a peptide having enzyme inhibiting activity, and more specifically, to a serine protease inhibitor extracted from animal tissues.

Research on inhibitors of trypsin and trypsin-like serine proteases dates back long ago. Many protease inhibitors have been isolated from the blood and endocrine secretions of mammals, snake venom and plants such as beans, and their properties elucidated. Research results on protease inhibitors are described in detail in, for example, the following literature references.

(1) Methods in Enzymology, vol. XLV, pp. 751–881, edited by Laszlo Lorand, Academic Press, 1976

(2) Biochemistry Data Book I, pp. 225–231, edited by Japanese Biochemical Society, Tokyo Kagaku Dojin, 1979

It is well known that many diseased conditions such as inflammation and vessel wall disorders are caused by reactions such as blood coagulation and kinin formation which are catalyzed by serine proteases in the blood or tissues [N. Heinburger, "Proteinase Inhibitor" by H. Fritz et al., Springer-Verlag, Berlin, pp. 14–22 (1974)].

Accordingly, specific inhibitors of these enzymes can be used to inhibit or remedy development of diseased conditions such as blood congestion and edema accompanied by inflammation, and vascular troubles involving fibrinoid degeneration caused by collagen diseases, Bechet's disease and so on.

The above inhibitors of trypsin and trypsin-like proteases, however, do not have so high a specificity for the enzymes in tissues as to be used as drugs. In order to solve this problem, the present inventor extensively searched for inhibitors of serine protease having high specificity for mammals, particularly those of trypsin or an enzyme analogous to trypsin (to be referred to as "trypsin-like serine protease"), and succeeded in isolating a serine protease inhibitor having a novel structure from the tissues, such as liver, lungs and tongue, of rats.

The inhibitor of this invention is a novel basic peptide having a molecular weight of about 7,600 and the following amino acid sequence:

Ile—Ala—Ala—Cys—Asn—Leu—Pro—Ile—Val—Gln—Gly—
Pro—Cys—Arg—Ala—Phe—Ala—Glu—Leu—Leu—Ala—Phe—
Asp—Ala—Ala—Gln—Gly—Lys—Cys—Ile—Gln—Phe—Ile—
Tyr—Gly—Gly—Cys—Lys—Gly—Asn—Asn—Asn—Lys—Phe—
Tyr—Ser—Glu—Pro—Lys—Cys—Lys—Trp—Tyr—Cys—Gly—
Val—Pro—Gly—Asp—Gly—Tyr.

All residues in the above sequence are L-amino acids.

The inhibiting activity of the peptide of this invention is very strong and specific for trypsin and trypsin-like serine proteases such as tryptase, and when it is mixed with a serine protease in a mole ratio of 1:1, complete inhibition takes place immediately. Its inhibiting activity on chymase, an enzyme analogous to chymotrypsin, is very weak and is about 1/1,000 of that on trypsin. This peptide does not at all inhibit thiol proteases such as cathepsins B, H and L and acid proteases such as cathepsin D, all of which are not serine proteases. Thus, the enzyme inhibiting activity of the peptide of this invention is highly specific for trypsin and trypsin-like serine proteases.

The peptide of this invention having serine protease inhibiting activity can be produced and purified from extracts of tissues, such as liver, lungs and tongue, of rats, for example by the following procedure. The above tissue is homogenized in an aqueous sodium chloride solution containing EDTA. Trichloroacetic acid is added to adjust the pH to 2.0. The homogenate is then stirred and centrifuged to obtain a supernatant. The precipitate is re-extracted by homogenization with the same buffer, and centrifuged to obtain a supernatant. The two supernatants are combined, and adjusted to pH about 8.5 with alkali. Tris-HCl buffer (pH 8.5) is added to a final concentration of about 10 mM. The mixture is applied to a column of Trypsinogen-Sepharose 4B and fractions containing enzyme inhibiting activity is eluted with an acidic sodium chloride solution. The fractions are then concentrated by ultrafiltration. The concentrated sample is then applied to a column of Sephadex G-75 equilibrated with a sodium acetate buffer. Fractions containing the desired peptide of this invention are collected and concentrated by, for example, ultrafiltration. The concentrated sample is subjected to HPLC on a reversed-phase column with a linear gradient of acetonitrile to collect fractions of the desired serine protease inhibiting peptide which gives a single band on SDS-polyacrylamide gel electrophoresis.

As stated above, the peptide of this invention has a very strong and specific inhibiting action on trypsin and trypsin-like serine proteases such as tryptase. Because of its strong and specific inhibiting activity on trypsin and trypsin-like serine proteases, the peptide of this invention is expected to be useful as a drug for inhibiting or remedying development of diseased conditions, for example blood congestion and edema accompanied by inflammation and vascular disorders involving fibrinoid degeneration caused by collagen disease and Bechet's disease.

For use as a serine protease inhibitor, the peptide of this invention may be formulated into a pharmaceutical preparation together with pharmaceutically acceptable adjuvants.

In the accompanying drawings,

FIG. 1 is a column chromatogram on Sephadex G-75 of an extract containing the peptide of this invention obtained from a rat liver sample; and FIG. 2 is an SDS-polyacrylamide gel electrophorogram of the peptide of this invention.

The following Example and Test Example illustrate the present invention more specifically.

EXAMPLE

About 500 g of fresh rat liver was added to 2,000 ml of 0.5 M sodium chloride solution containing 10 mM of EDTA and the mixture sufficiently homogenized by a superhigh speed homogenizer. Trichloroacetic acid was added to adjust the pH to 2.0. The homogenate was then stirred at a low temperature for 2 hours and centrifuged at 24,000 × g for 20 minutes to obtain a supernatant. The resulting precipitate was re-extracted by homogenization in 1,000 ml of the same buffer, stirred overnight at room temperature, and centrifuged at 24,000 × g for 20 minutes to obtain a supernatant.

The two supernatants were combined, and adjusted to pH 8.5 with a 10 N aqueous solution of sodium hydroxide. To this solution, a 1 M Tris-HCl buffer (pH 8.5) was added to a final concentration of 100 mM.

The resulting solution was applied to a 40 ml Trypsinogen-Sepharose 4B column which had been equilibrated with 100 mM Tris-HCl (pH 8.5) containing 0.5M sodium chloride at a flow rate of 60 ml/hr.

The column was washed with 1,000 ml of 0.5M sodium chloride solution and then developed with 20 mM hydrochloric acid solution containing 0.5 M sodium chloride to collect fractions containing trypsin inhibiting activity. These fractions were pooled, and concentrated on an ultrafiltration membrane (Amicon YM-2). The concentrated sample was applied to a Sephadex G-75 column (3 × 120 cm) which had been equilibrated with a 10 mM sodium acetate buffer (pH 5.0) containing 0.5M sodium chloride at a flow rate of 15 ml/hr.

As FIG. 1 shows, the enzyme inhibiting activity was separated into three peaks by gel filtration. Fractions of peak 3 having the lowest molecular weight were pooled and concentrated on an ultrafiltration membrane.

The concentrated sample was subjected to reversed phase high-performance liquid chromatography (Cosmosil 5C$_4$-300 produced by Nakarai Chemical Co., Ltd.) with a linear gradient of 0 to 90 % acetonitrile at a flow rate of 1.0 ml/min. Fractions containing enzyme inhibiting activity were pooled, concentrated by ultrafiltration, and again subjected to reversed phase high-performance liquid column chromatography under the same conditions. SDS-polyacrylamide gel electrophoresis of fractions with antitryptic activity by the method described in Nature, 227, pp. 680-685, 1970, Laemmli, U. K. gave a single band, and their molecular weight was estimated at 7,600±500.

The amino acid sequence of the trypsin inhibitor of this invention was determined by an Applied Biosystems gas-phase protein sequencer, Model 470A.

TEST EXAMPLE

The antitryptic activity of the sample obtained in Example 1 was measured by the following procedure.

A 100 mM Tris-HCl buffer (pH 8.5; 1.92 ml) was added to 10 microliters of 10 mM HCl solution of crystalline trypsin (1μg/ml, corresponding to 2.2m units, derived from porcine spleen, Type IX, Sigma Co.) and then 50 microliters of a sample solution was added. After incubation at 25° C. for 5 minutes, 10 microliters of a substrate solution (20 mM Boc-Phe-Ser-Arg.MCA, dissolved in dimethyl sulfoxide) was added to start the reaction. The amount of MCA (7-amino-4-methylcoumarine) liberated was directly measured (emission 460 nm, excitation 380 nm) by a spectrofluorometer (Model 950-10S made by Hitachi Limited).

One inhibitory unit was defined as the amount of the inhibitor which decreased the trypsin activity by one unit.

I claim:

1. A peptide having an amino acid sequence of the following formula:

Ile—Ala—Ala—Cys—Asn—Leu—Pro—Ile—Val—Gln—Gly—
Pro—Cys—Arg—Ala—Phe—Ala—Glu—Leu—Leu—Ala—Phe—
Asp—Ala—Ala—Gln—Gly—Lys—Cys—Ile—Gln—Phe—Ile—
Tyr—Gly—Gly—Cys—Lys—Gly—Asn—Asn—Asn—Lys—Phe—
Tyr—Ser—Glu—Pro—Lys—Cys—Lys—Trp—Tyr—Cys—Gly—
Val—Pro—Gly—Asp—Gly—Tyr said peptide having sufficient purity to give a single band on SDS-polyacrylamide gel electrophoresis.

2. The peptide of claim 1 in which all residues in the sequence are L-amino acids.

3. A peptide serine protease inhibitor composition comprising a peptide having an amino acid sequence of the following formula:

Ile—Ala—Ala—Cys—Asn—Leu—Pro—Ile—Val—Gln—Gly—

Pro—Cys—Arg—Ala—Phe—Ala—Glu—Leu—Leu—Ala—Phe—

Asp—Ala—Ala—Gln—Gly—Lys—Cys—Ile—Gln—Phe—Ile—

Tyr—Gly—Gly—Cys—Lys—Gly—Asn—Asn—Asn—Lys—Phe—

Tyr—Ser—Glu—Pro—Lys—Cys—Lys—Trp—Tyr—Cys—Gly—

Val—Pro—Gly—Asp—Gly—Tyr said peptide having sufficient purity to give a single band on SDS-polyacrylamide gel electrophoresis; and a pharmaceutically acceptable adjuvant.

4. The peptide of claim 1 which is isolated from a rat tissue.

* * * * *